(12) United States Patent
Schneider

(10) Patent No.: US 10,307,702 B2
(45) Date of Patent: *Jun. 4, 2019

(54) FILTERS WITH ODOR-CONTROLLING COMPOSITIONS

(71) Applicant: Rem Brands, Inc., Walton, KY (US)

(72) Inventor: David J. Schneider, Union, KY (US)

(73) Assignee: REM BRANDS, INC., Walton, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/674,900

(22) Filed: Aug. 11, 2017

(65) Prior Publication Data

US 2017/0340998 A1  Nov. 30, 2017

Related U.S. Application Data

(63) Continuation-in-part of application No. 15/019,879, filed on Feb. 9, 2016, now Pat. No. 9,987,389, which
(Continued)

(51) Int. Cl.
*A61K 8/46* (2006.01)
*A61L 9/01* (2006.01)
(Continued)

(52) U.S. Cl.
CPC ............ *B01D 39/14* (2013.01); *A61K 8/466* (2013.01); *A61L 9/01* (2013.01); *A61L 9/16* (2013.01);
(Continued)

(58) Field of Classification Search
None
See application file for complete search history.

(56) References Cited

U.S. PATENT DOCUMENTS

| 9,987,389 B2 * | 6/2018 | Schneider | A61L 15/46 |
| 2006/0280766 A1 * | 12/2006 | Schneider | A01N 41/08 |
|  |  |  | 424/405 |
| 2007/0175196 A1 * | 8/2007 | Tepper | B01J 20/08 |
|  |  |  | 55/527 |

* cited by examiner

*Primary Examiner* — Aradhana Sasan
(74) *Attorney, Agent, or Firm* — Fay Sharpe LLP

(57) ABSTRACT

A filter is treated with a reduced amount of a halo active aromatic sulfanomide compound of Formula (I):

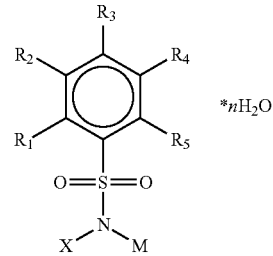

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl; R' is hydrogen, an alkali metal, an alkaline earth metal, substituted $C_1$-$C_{12}$ alkyl, or unsubstituted $C_1$-$C_{12}$ alkyl; and R" is hydrogen or substituted or unsubstituted $C_1$-$C_{12}$ alkyl, where the two R" groups in CON(R")$_2$ may be independently selected; X is halogen; M is an alkali or alkaline earth metal; and n is the number of water molecules per molecule of the sulfonamide compound. The compound effectively suppresses odors pre-use, in use, and post-use for extended periods of time.

21 Claims, 7 Drawing Sheets

Related U.S. Application Data is a continuation-in-part of application No. 13/105,954, filed on May 12, 2011, now Pat. No. 9,539,446.

(60) Provisional application No. 62/374,604, filed on Aug. 12, 2016, provisional application No. 62/113,768, filed on Feb. 9, 2015, provisional application No. 61/334,678, filed on May 14, 2010.

(51) Int. Cl.

| | |
|---|---|
| *A61L 9/16* | (2006.01) |
| *A61Q 5/02* | (2006.01) |
| *A61Q 5/06* | (2006.01) |
| *C02F 1/00* | (2006.01) |
| *C02F 1/28* | (2006.01) |
| *A61L 15/46* | (2006.01) |
| *A61Q 17/04* | (2006.01) |
| *A61Q 19/00* | (2006.01) |
| *B01D 39/14* | (2006.01) |
| *B01D 46/00* | (2006.01) |
| *B01D 46/10* | (2006.01) |
| *B01D 46/12* | (2006.01) |
| *B01D 46/52* | (2006.01) |
| *B01J 20/22* | (2006.01) |
| *B01J 20/28* | (2006.01) |
| *B01J 20/32* | (2006.01) |

(52) U.S. Cl.
CPC .............. *A61L 15/46* (2013.01); *A61Q 19/00* (2013.01); *B01D 46/0038* (2013.01); *B01D 46/125* (2013.01); *B01D 46/525* (2013.01); *B01J 20/22* (2013.01); *B01J 20/28035* (2013.01); *B01J 20/321* (2013.01); *B01J 20/3204* (2013.01); *B01J 20/3212* (2013.01); *B01J 20/3253* (2013.01); *A61K 2800/10* (2013.01); *A61L 2209/14* (2013.01); *A61Q 5/02* (2013.01); *A61Q 5/06* (2013.01); *A61Q 17/04* (2013.01); *B01D 46/10* (2013.01); *B01D 2239/045* (2013.01); *B01D 2279/50* (2013.01); *C02F 1/001* (2013.01); *C02F 1/285* (2013.01); *C02F 2303/02* (2013.01)

FILTERS WITH ODOR-CONTROLLING COMPOSITIONS

CROSS-REFERENCE TO RELATED APPLICATIONS

This application claims priority to U.S. Provisional Patent Application Ser. No. 62/374,604, filed Aug. 12, 2016. This application is also a continuation-in-part of U.S. patent application Ser. No. 15/019,879, filed Feb. 9, 2016, which claimed priority to U.S. Provisional Patent Application Ser. No. 62/113,768, filed Feb. 9, 2015, and was also a continuation-in-part of U.S. patent application Ser. No. 13/105,954, filed on May 12, 2011, which claimed priority to U.S. Provisional Patent Application Ser. No. 61/334,678, filed May 14, 2010. These applications are fully incorporated by reference herein.

BACKGROUND

The present disclosure relates to filters treated with sulfonamide compounds having odor control characteristics. This removes odors in fluid streams passing through the filters, such as liquid or gas streams, removing undesirable odors.

Filters, such as air and water filters, find widespread use in industrial and commercial applications that have certain requirements for air and water. Such filters may be incorporated in a filtration system, and a fluid stream is forced through the filter. Fluid streams include liquid streams (e.g. water) and gas streams (e.g. air). Such fluid streams can contain contaminants as a result of upstream processes, storage, usage, dust and debris from the surrounding environment, etc. Often, it is generally desirable to remove such contaminants from fluid streams for comfort, aesthetics, reduction of damage to downstream components, or environmental safety, for example. Additionally, these contaminants may have an unpleasant odor (malodor) due to odor-causing molecules which may be aliphatic, aromatic, or heterocyclic compounds containing oxygen, sulfur, or nitrogen.

The odor-causing (odorific) molecules can be masked using a more pleasant smelling molecule, such as a perfume. However, it would be desirable to alter, neutralize, and/or destroy the odorous molecule instead.

BRIEF DESCRIPTION

Disclosed herein, in various embodiments, are filters that can be used to destroy odorific molecules in a fluid. This combines the odor-destroying function with the cleaning function of the filter, reducing the space/volume and equipment which must otherwise be used to achieve both functions. In particular, the filters of the present disclosure use sulfonamide compounds which can neutralize and/or destroy odor-causing molecules that are generated/released over an extended period of time.

The filters of the present disclosure are a porous substrate made from one or more layers of a filter medium. Contained within the one or more layers of the filter medium is a halo active aromatic sulfonamide compound according to Formula (I), shown herein.

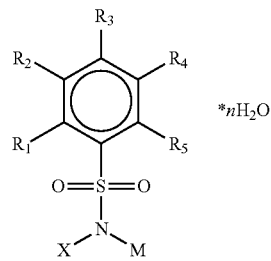

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;

R' is hydrogen, an alkali metal, an alkaline earth metal, substituted $C_1$-$C_{12}$ alkyl, or unsubstituted $C_1$-$C_{12}$ alkyl; and R" is hydrogen or substituted or unsubstituted $C_1$-$C_{12}$ alkyl, where the two R" groups in CON(R")$_2$ may be independently selected;

X is halogen;

M is an alkali or alkaline earth metal; and n is the number of water molecules per molecule of the sulfonamide compound.

In particular embodiments, the filter includes a porous substrate made from one or more layers of a filter medium which has the halo active aromatic sulfonamide compound of Formula (I) dispersed thereon. In some particular embodiments, the halo active aromatic sulfonamide compound is not chloramine-T (where $R_3$=CH$_3$ and $R_1$=$R_2$=$R_4$=$R_5$=H).

It is contemplated that the halo active aromatic sulfonamide compound is present in the amount of about 0.0001 to about 10.0 grams per gram of the substrate.

In yet more embodiments, the filter medium is made from a natural material, an inorganic material, a synthetic material, or a mixture thereof. The filter medium can be woven or nonwoven.

In particular embodiments, the filter medium is formed from regenerated fiber of a cellulosic material including wet-laid media, acetate, triacetate, rayon, or lyocell.

In particular embodiments, the filter medium fiber is a polymeric material including polyvinyl chloride (PVC), polyethylene (PE), polypropylene (PP), fluoropolymer, polytetrafluoroethylene (PTFE), polyethersulfone (PES), nylon, acrylic, polyester, polyolefin, polyvinylidene difluoride (PVDF), polyphenylene sulfide (PPS), polyetherimide (PEI), polyether ether ketone (PEEK), liquid crystal polymer (LCP), aramid fiber, or polyimide fiber.

In more embodiments, the filter medium is made from metal, fiberglass, glass, or stainless steel. In other embodiments, the filter medium is made cotton, needle-felt fabric, or rubber. It is contemplated that the halo active aromatic sulfonamide compound may be in the form of a solid or is encapsulated in a water-soluble medium. The solid or encapsulated halo active aromatic sulfonamide compound can be disposed within a flexible housing formed by the one or more layers of filter medium that make up the porous substrate, forming a packet. The porous substrate may be pleated or flat. The filter may further comprise a support frame engaging the porous substrate. The sulfonamide compound can be applied to the filter medium/porous substrate in the form of a solution, in which the sulfonamide compound is present in an amount from about 0.01% to 30% (w/v).

Also disclosed are methods of reducing odor in fluid stream, comprising passing a fluid stream containing odorific molecules through a filter which contains the halo active aromatic sulfonamide compound of Formula (I).

The fluid stream may be a liquid fluid stream or a gas fluid stream.

In particular embodiments, the odor is reduced over a life span of the filter. This may be measured in weeks, months, or years. In particular, sulfur-containing odorific molecules and/or nitrogen-containing odorific molecules present in the fluid stream are reduced/destroyed.

In some embodiments, the filter medium is a nonwoven natural, inorganic, or synthetic material. In other embodiments, the filter medium is a woven natural, inorganic, or synthetic material.

It is also contemplated that the filter medium captures particles having a size of about 2000 micrometers ($\mu m$), or from about 70 $\mu m$ to about 2000 $\mu m$, or from about 0.1 $\mu m$ to about 70 $\mu m$, or from about 0.1 $\mu m$ to about 1 $\mu m$, or from about 0.005 $\mu m$ to about 0.1 $\mu m$, or from about 0.001 $\mu m$ to about 0.005 $\mu m$, or about 0.001 $\mu m$.

Also disclosed are filtration systems comprising a fluid duct which transports a fluid stream containing odorous molecules, and a filter disposed within the fluid duct. The fluid stream passes through the filter. The filter includes a porous substrate made from one or more layers of a filter medium, and a halo active aromatic sulfonamide compound contained within the filter, the halo active aromatic sulfonamide compound having the structure of Formula (I).

In some embodiments, the filter medium is a nonwoven natural, inorganic, or synthetic material. In other embodiments, the filter medium is a woven natural, inorganic, or synthetic material.

In other embodiments, the filter includes a plurality of porous substrates, with at least one of the porous substrates having the halo active aromatic sulfonamide compound contained therein. Generally, however, each porous substrate is treated with the halo active aromatic sulfonamide compound.

It is also contemplated that the fluid duct and the filter are located in an HVAC unit or system, an automobile, a water filtration unit or system, an industrial or commercial filtration unit or system, a vacuum cleaner or other commercial or household cleaning device.

These and other non-limiting features or characteristics of the present disclosure will be further described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1A:
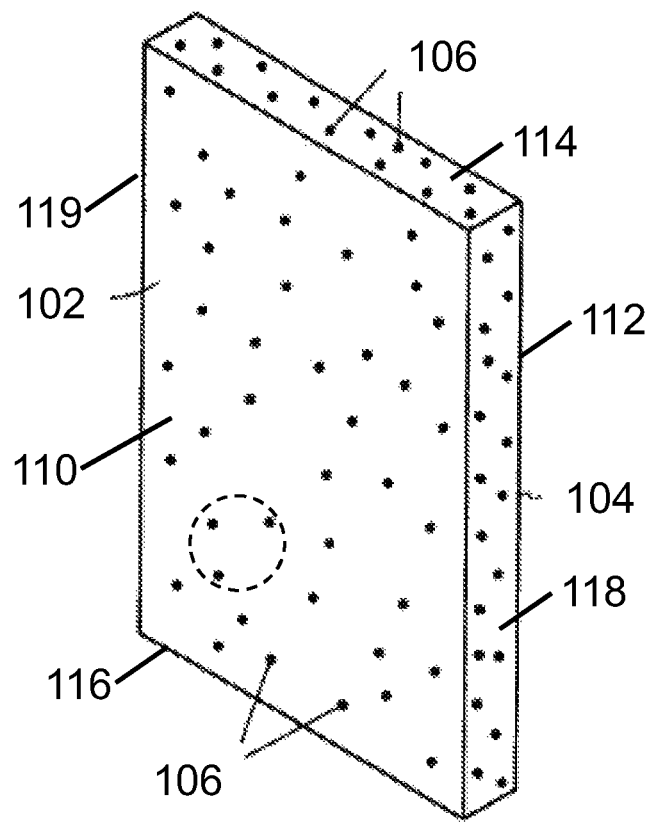
FIG. 1A illustrates a porous substrate containing the halo active aromatic sulfonamide compounds of the present disclosure.

A more complete understanding of the components, processes, and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

The term "fluid", as used herein, refers to both liquids and gases, and also to solids.

As used herein, a "fluid duct" refers to a housing or similar structure that can contain a fluid, such as a liquid or a gas, and transport the fluid between two different locations. The fluid duct may have one or more inlets, and may have one or more outlets. It is contemplated that this term includes air ducts and vents that are known for use in residences, commercial buildings, vehicles (e.g. automobiles, trains, airplanes, etc.); and pipes for carrying fluids such as water. Such fluid ducts are typically part of a larger heating/cooling system. The fluid duct can include structures for controlling the intake/output of the fluid, such as valves, etc.

The term "wetlaid" refers to a process for forming nonwoven textiles, where short material fibers are suspended in a fluid, the fibers are deposited onto a screen or porous surface to remove the fluid, and the web is then consolidated mechanically, chemically, or thermally.

The term "drylaid" refers to a process for forming nonwoven textiles, where staple material fibers are processed into fibrous webs. The processing can be performed by air laying ("airlaid") or by carding. Air-laid textiles have a randomly oriented fibrous web produced by short fibers dispersed in air by various means to produce a "cloud" of fibers within a chamber. The fibers are then transported through the air toward a permeable conveyor belt under which suction is applied. The suction gathers the fibers onto the conveyor surface where the web can be formed either mechanically, chemically, or thermally. Carded textiles have an oriented fibrous web produced from bales of long staple fibers. The bales are opened and fed to a carding machine which combs the fibers into a desired web configuration. The web can then be formed either mechanically, chemically, or thermally.

The term "spunlaid" or "spunbond" refers to a process for forming nonwoven textiles where polymer granules are melted and molten polymer is extruded through spinnerets. The continuous filaments are cooled and deposited on to a conveyor to form a uniform web.

The term "meltblown" refers to a process for forming nonwoven textiles where low viscosity polymers are extruded into a high velocity airstream upon leaving a spinneret. This scatters the melt, solidifies it and breaks it up into a fibrous web.

The term "parallel" should be construed in a layman's manner as two edges or faces generally continuously having the same distance between them, and should not be strictly construed in mathematical terms as requiring that the two edges or faces cannot intersect when extended for an infinite distance.

Halo active aromatic sulfonamide organic compounds are known. Chloramine-T is an example of a sulfonamide organic compound which has been used in many applications. The usefulness of Chloramine-T is predicated on its ability to release an active Cl+ ion when needed on demand, immediately after which, it simultaneously generates an active aromatic sulfo nitrene companion ion. The active Cl+ ion and the companion aromatic sulfo nitrene ion may work together to degrade odor-causing molecules. The term "Cl+" refers to the fact that the chlorine atom has a +1 formal charge in a hypochlorite ion, ClO$^-$, which is the form taken by the chlorine atom when dissociated from the sulfonamide compound. A chlorine atom is generally considered to have a charge of 1$^-$. Reference to the chlorine atom as having a +1 or 1$^-$ charge may be used in this application interchangeably because this terminology has no effect on the compound itself or its use.

Most odor causing molecules are mercaptans, sulfides, heterocyclic or amine based compounds. Halo active aromatic sulfonamide compounds are excellent agents for eliminating odors from these classes of compounds as both the Cl+ cations and the sulfonamide moiety remaining after the Cl+ cations are produced, react with the odor causing molecule(s).

The filters of the present disclosure generally comprise (i) a porous substrate made of one or more layers of a filter medium or material that are fluid-permeable; and (ii) a halo active aromatic sulfonamide compound, as described further herein. The filters can be used with additional components which together make up a filtration system. The halo active aromatic sulfonamide compound can be applied to the filter medium or the porous substrate in the form of an odor-controlling composition, or in other words, the odor-controlling composition can be generally contained within or throughout the porous substrate or filter medium. The halo active aromatic sulfonamide compound can also be applied to other parts of the filter.

The porous substrate includes pores extending therethrough between opposite surfaces of the porous substrate. The pores block certain materials from passing through the pores while letting others through (i.e. to serve a filtering function). The filtering function can be performed by size, adsorption, or other properties. The porous substrate is formed from one or more layers of a filter medium. The filter medium can be made from fibrous materials. The fibrous materials may or may not be absorbent. The filter medium can also be made from foam. The substrate may be of any desired size and shape, depending on the application for which a particular filter is used. In various embodiments, the porous substrate is flat or is pleated. A support frame may be used to support the porous substrate. The porous substrate can be shaped as desired for its intended use/purpose/application. For example, the porous substrate can be made in a flat panel, tubular, cylindrical, or bag form. The porous substrate may be used in a filter such as, for example, an HVAC or HEPA filter for residential or commercial use, a microporous membrane filtration media, or any other filter providing a fluid-permeable, porous substrate useful for removing contaminants from a fluid (e.g., air or water).

At least one halo active aromatic sulfonamide compound is contained within at least one layer of the filter medium/media used to form the porous substrate. The term "contain" and its different forms (e.g. contained, containing) are hereby defined to include all possible locations on or in the filter medium that the sulfonamide compound can be deposited upon or within, e.g. on the outer surface of the filter medium, within the filter medium, voids formed by the filter medium, etc. For example, when the filter medium is made of a fibrous material, the term "contained" is intended to include locations on the surface of the fiber, in voids between fibers, and within the fiber itself if the fiber is absorbent. As another example, if the filter medium is made from foam, the term "contained" also includes locations within the pores of the foam. The term "contained" is also intended to encompass forms in which the porous substrate surrounds the sulfonamide compound. It is specifically contemplated that the halo active aromatic sulfonamide compound is used in the form of a dry powder, but the compound is also effective when wet.

The filter can be made from one or more layers of a filter medium. The filter is typically dry, i.e. not moist like a wipe. A fluid stream passes through the filter, and odorous molecules in the fluid stream react with the active sulfonamide compound on the substrate.

FIG. 1A illustrates a flat panel porous substrate 102 that may be used with the filters of the present disclosure. The porous substrate 102 is formed from one or more layers of a filter medium 104. The porous substrate 102/filter medium 104 contains a halo active aromatic sulfonamide organic compound 106 contained therein. The substrate is in the form of two large surfaces 110, 112, which are spaced apart from each other and define opposite sides of the substrate. The two surfaces 110, 112 are parallel to each other, and are flat (i.e. the substrate has a constant thickness). The substrate also includes a top surface 114 and a bottom surface 116 which are spaced apart from and parallel to each other. The substrate also includes a first side surface 118 and a second side surface 119 which are spaced apart from and parallel to each other.

Figure 1B:
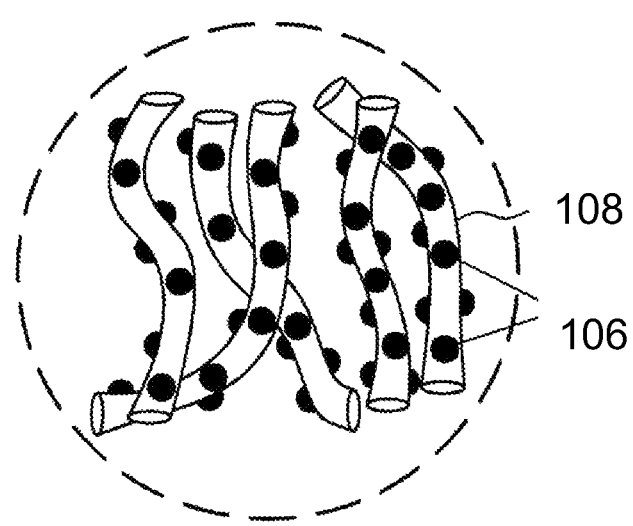
FIG. 1B is a magnified view illustrating individual fibers of the porous substrate having the halo active aromatic sulfonamide compound dispersed thereon.

FIG. 1B is a magnified view of a section of FIG. 1A showing a plurality of fibers 108 which make up the filter medium 104. The fibers 108 are an example of a material from which the filter medium can be made, and upon which the halo active aromatic sulfonamide organic compound 106 is contained. Again, this means the halo active aromatic sulfonamide organic compound 106 may be embedded on the surface of the fibers 108, or filling some of the voids between the fibers.

Figure 2:
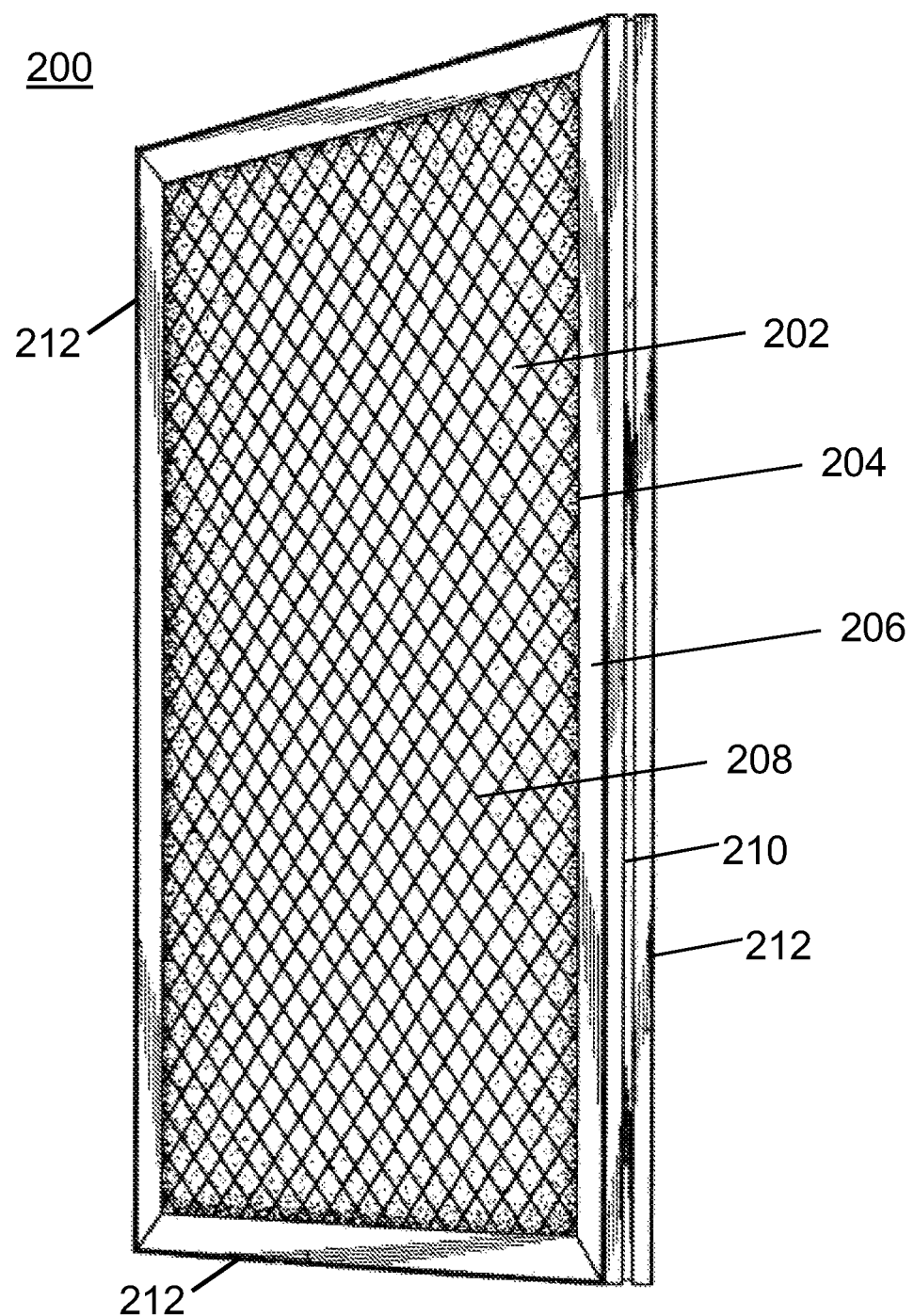
FIG. 2 is a perspective view of an air filter containing the porous substrate having the halo active aromatic sulfonamide compounds of the present disclosure dispersed thereon and being useful for residential, commercial, or industrial HVAC systems.

It should be noted that the porous substrate is generally only one part of the overall filter. As shown in FIG. 2, the air filter 200 includes a porous substrate 202 having one or more layers of a filter medium 204. A frame 206 receives the porous substrate 202 therein. The porous substrate 202 can be described as filling the interior area of the frame 206. Each of the outer edges (not shown) of the porous substrate 202 is typically compressively received within the frame 206. The frame 206 has a generally rectangular configuration, the specific size of which is dependent upon the requirements of the HVAC system into which it is to be used. However, it should be understood that the present disclosure should not be limited by particular shapes/sizes identified for the filter/frame, and that the filter can have any suitable shape/size depending on the application with which it is to be used.

Here, the frame 206 can be described as having an interior groove into which the porous substrate 202 fits. The frame has two large openings that align with the two large surfaces of the porous substrate 202. In this case, the frame also has an exterior groove 210 on the outer side surfaces 212 of the frame itself, along the center of the outer side surfaces.

The filter 200 can include additional support structures for the porous substrate 202, such as a first flexible mesh layer 208 on one side of the porous substrate and a second flexible mesh layer (not visible) on the opposite side. The porous substrate 202 is sandwiched between the first and second flexible mesh layers. The flexible mesh layers themselves can be made from any suitable material, such as an extruded polymeric material (e.g., polypropylene) or a metallic material (e.g., stainless steel).

The porous substrate 202 generally contains the halo active aromatic sulfonamide organic compound dispersed on or within the one or more layers of the filter medium 204. In addition, the halo active aromatic sulfonamide organic compound can be dispersed on the other support structures of the HVAC filter 200, including the mesh support layer 208. This may occur, for example, if the aromatic sulfonamide compound is sprayed onto the filter after the porous substrate 202 and frame 206 are combined. As a fluid stream, typically air in this case, passes through the filter 200 and over the other filter components, odorous molecules in the fluid stream react with the active sulfonamide compound, thereby reducing and eventually eliminating the odor of the fluid stream. Furthermore, the odor of the contaminants/particles which are trapped in the filter 200 or other components will be reduced and eventually eliminated.

Figure 3:
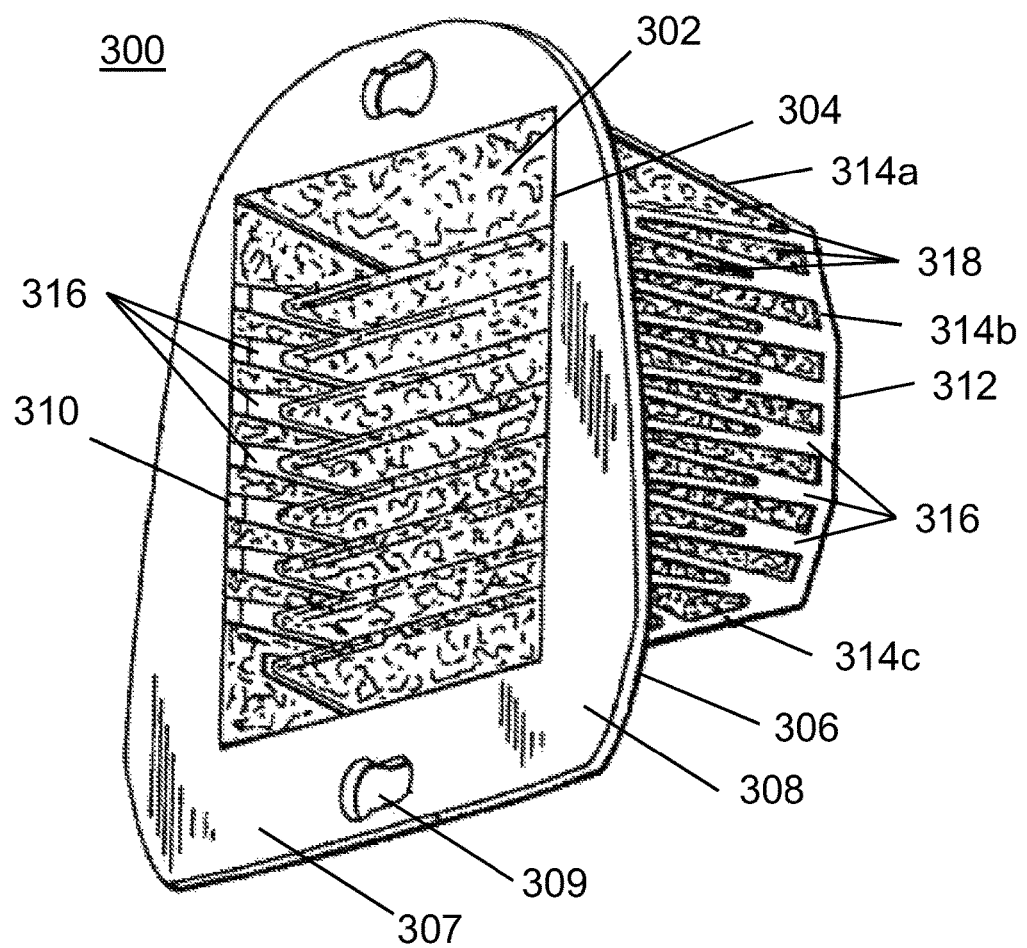
FIG. 3 is a perspective view of an air filter containing the porous substrate having the halo active aromatic sulfonamide compounds of the present disclosure dispersed thereon and being useful for consumer appliances such as vacuum cleaners.

As another example, the porous substrate may be included in a filter for use in a consumer appliance, such as a vacuum cleaner, which is used for general cleaning purposes (e.g., dirt associated with pets). Referring to FIG. 3, an air filter 300 includes a porous substrate 302. A molded frame 306 supports the porous substrate 302, which is formed from a filter medium 304, and has a pleated shape. The molded frame 306 comprises a flat surface 308 and two opposing side support frames 310, 312 extending transverse to the flat surface. The flat surface has a central opening therein which provides access to the porous substrate 302. The remainder of the flat surface forms a rim 307, illustrated here with two holes 309 that allow the filter to engage the appliance. Each side support frame 310, 312 comprises an outer frame 314a, 314b, 314c within which are formed an array of support arms 316 which co-operate in a zig-zag formation to support the pleated filter medium 304. The pleated filter medium is also supported by the end support arms 314a, 314c of the outer frame. In addition, triangular shaped sections 318 of filter medium are supported between adjacent support arms 316a, adjacent support arms 316b, adjacent support arms 314a, 316, and adjacent support arms 314c, 316. These triangular sections 318 of filter medium 304 provide a side filter surface across the area contained within the outer frame 314a, 314b, 314c of each support frame 310, 312.

The porous substrate 302 generally contains the halo active aromatic sulfonamide organic compound dispersed on or within the one or more layers of the filter medium 304, including triangular shape sections 318. The halo active aromatic sulfonamide organic compound can be dispersed on the other support structures of the consumer appliance filter 300, including the frame 306, side support frames 310, 312, outer frame 314, and forked support arms 316. As a fluid stream, typically air in this case, passes through the filter 300 and over the other filter components, odorific molecules in the fluid stream react with the active sulfonamide compound, thereby reducing and eventually eliminating the odor of the fluid stream. Furthermore, the odor of the contaminants/particles which become trapped in the filter 300 or other components will be reduced and eventually eliminated.

Figure 4:
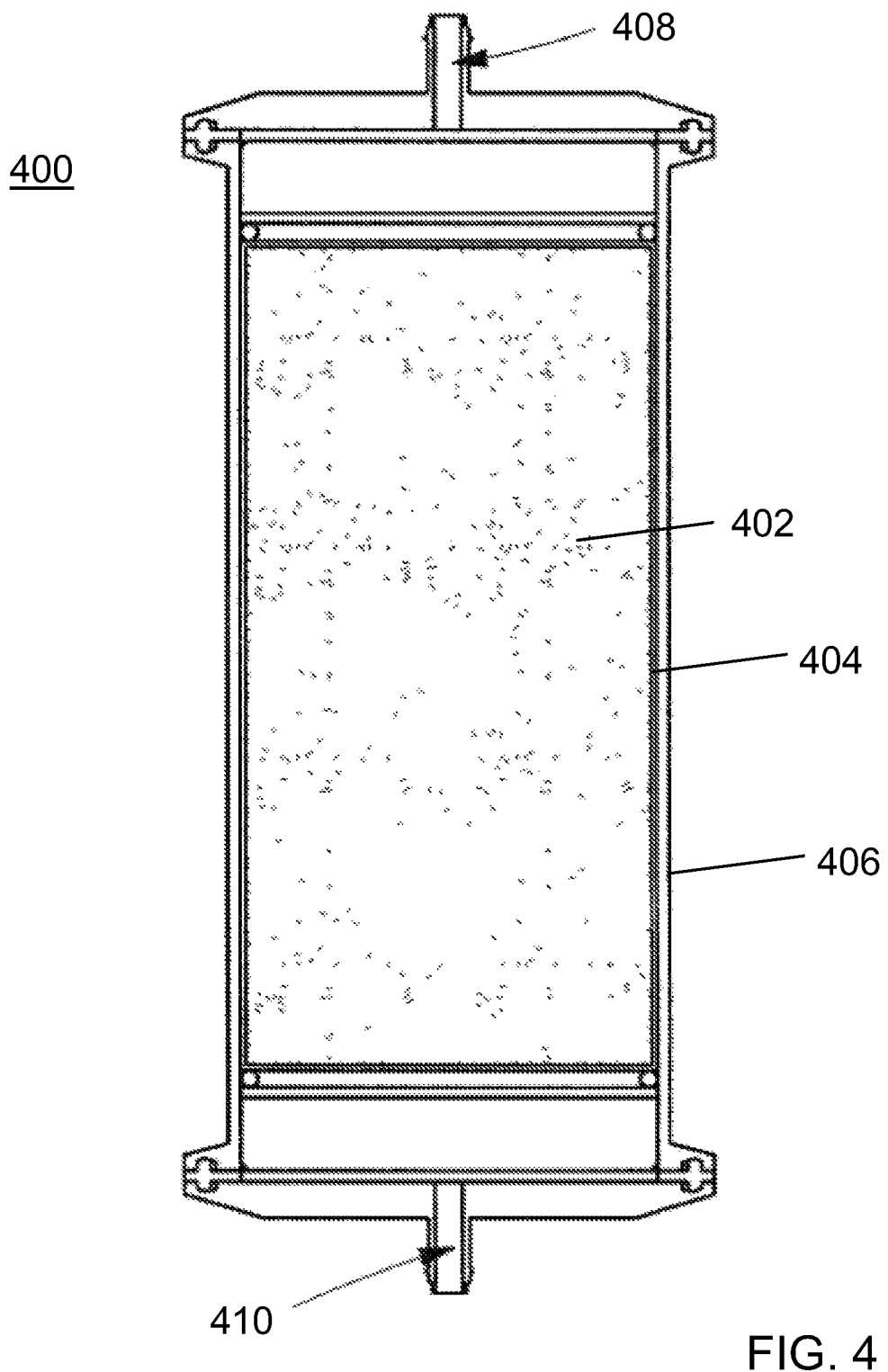
FIG. 4 is a cross-sectional side view of a water filter containing the porous substrate having the halo active aromatic sulfonamide compounds of the present disclosure dispersed thereon and being useful for water filtration systems.

As yet a further example, the porous substrate may be used as a water filter. FIG. 4 is a cross-sectional view of a water filter 400. The housing 406 of the filter 400 is in the form of a cylinder having an inlet 408 and an outlet 410, generally at opposite ends of the housing, though this is not required depending on the fluid flow path within the housing. The housing 406 can be provided in a variety of forms, shapes, sizes, and arrangements depending upon the intended use of the filter, as known in the art. For example, the filter can be an axial flow filter, wherein the inlet and outlet are disposed so that the liquid flows axially from the inlet through the porous substrate to the outlet. Alternatively, the filter can be a radial flow filter wherein the porous substrate is arranged in the form of a cylinder with an interior volume, and fluid flows radially. For example, the inlet provides fluid to the interior volume of the cylinder and liquid flow through the porous substrate to the exterior volume, which then leads to the outlet. The size, shape, spacing, alignment, and positioning of the inlet 408 and outlet 410 can be selected, as known in the art, to accommodate the flow rate and intended use of the filter 400. The housing may also be formed as part of another structure without departing from the scope of the present disclosure.

The housing 406 includes a porous substrate 402 formed from one or more layers of a filter medium 404, which contains the halo aromatic sulfonamide compound. In this particular embodiment, the filter medium is in the form of small solid grains, with the sulfonamide compound usually upon the surface thereof. The fluid stream passes through this filter by flowing through the voids around the grains. In addition, the halo active aromatic sulfonamide organic compound can be dispersed on the interior wall of the housing 406 as well. As a fluid stream, typically water in this case, passes through the filter 400 and over the other filter components, odorific molecules (e.g., sulfur-containing molecules and/or nitrogen-containing molecules) in the fluid stream react with the active sulfonamide compound, thereby reducing and eventually eliminating the odor of the fluid stream. Furthermore, the odor of the contaminants/particles which become trapped in the filter 400 or other components will be reduced and eventually eliminated.

Figure 5A:
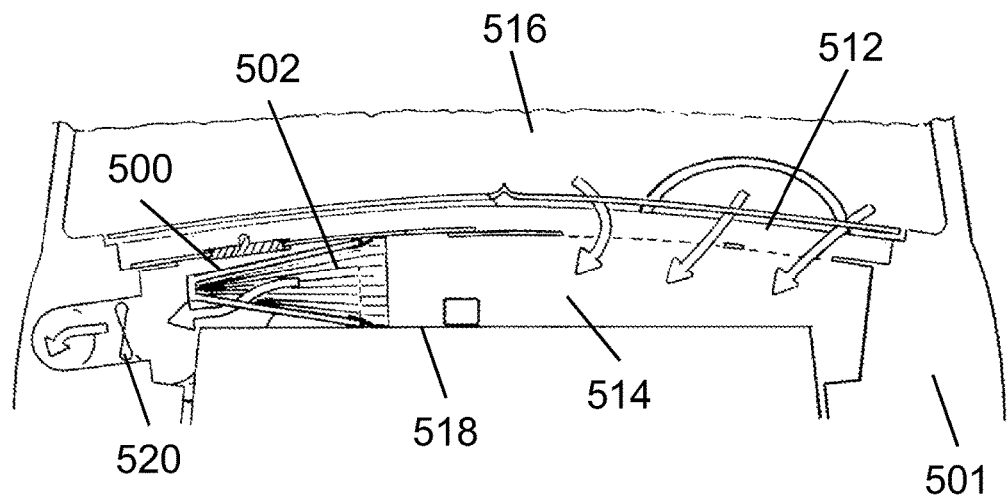
FIG. 5A is a side view illustrating an automotive air filtration system for an automobile interior in which an air filter can be used.
Figure 5B:
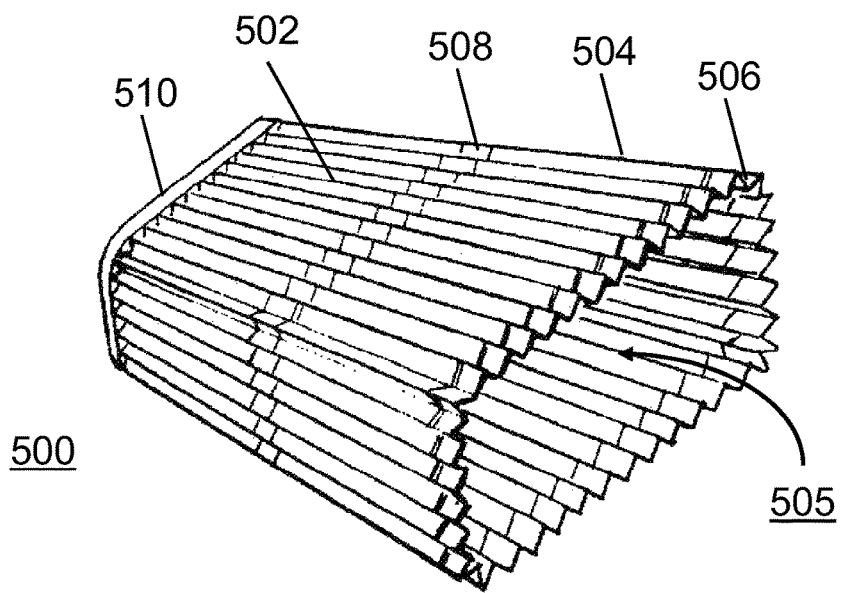
FIG. 5B is a perspective view of an air filter containing the porous substrate having the halo active aromatic sulfonamide compounds of the present disclosure dispersed thereon.

Another example depicted in FIG. 5A and FIG. 5B shows a filter 500 including a porous substrate 502 for use in a vehicle 501. The porous substrate 502 includes one or more layers of a filter medium 504.

The filter 500 illustrated in FIG. 5A is shown in a single cone, cartridge type configuration suitable for installation in a vehicle. The filter 500 is installed in an air-intake region 512 of an automobile where outside air enters an intake opening 514 located across the base of the windshield 516. The incoming outside air enters the intake 514 as indicated by the flow arrows in FIG. 5A and thereafter is confined for further entry through a duct 518 and into the filter 500. The filtered air thereafter flows to the fan 520 where it is pressurized and commences its distribution to the passenger compartment of the vehicle 501.

FIG. 5B illustrates additional details of the filter 500, including the pleated construction of the porous substrate 502. The porous substrate is in the form of a pleated sheet that is wrapped into a rectangular configuration around an interior volume 505, then closed at one end. At the open end of the porous substrate 502, a sealing tape 506 is secured in part to the entry portions of the filter cartridge 500. A stiffening band 508 can be included midway along the axial length of the filter. Such stiffening bands undergo the compaction and the expansion of the porous substrate 502 and help to maintain a desired configuration of the filter. A closed end portion 510 is used to secure the converging one or more layers of filter medium 504, such as with adhesives or adhesive suitable fastening means, to ensure that the fluid stream (i.e. air) flows through the porous substrate instead of around it.

The porous substrate 502 generally contains the halo active aromatic sulfonamide organic compound dispersed on or within the one or more layers of the filter medium 504. In addition, the halo active aromatic sulfonamide organic compound can be dispersed on the other components associated with the filter 500, including the portions of the seal 506, stiffening band 508, and closed end portion 510 that are present in the interior volume 505. As a fluid stream, typically air in this case, passes through the filter 500, odorific molecules in the fluid stream react with the active sulfonamide compound, thereby reducing and eventually eliminating the odor of the fluid stream. Furthermore, the odor of the contaminants/particles which are trapped in the filter 500 or other components will be reduced and eventually eliminated.

Figure 6:
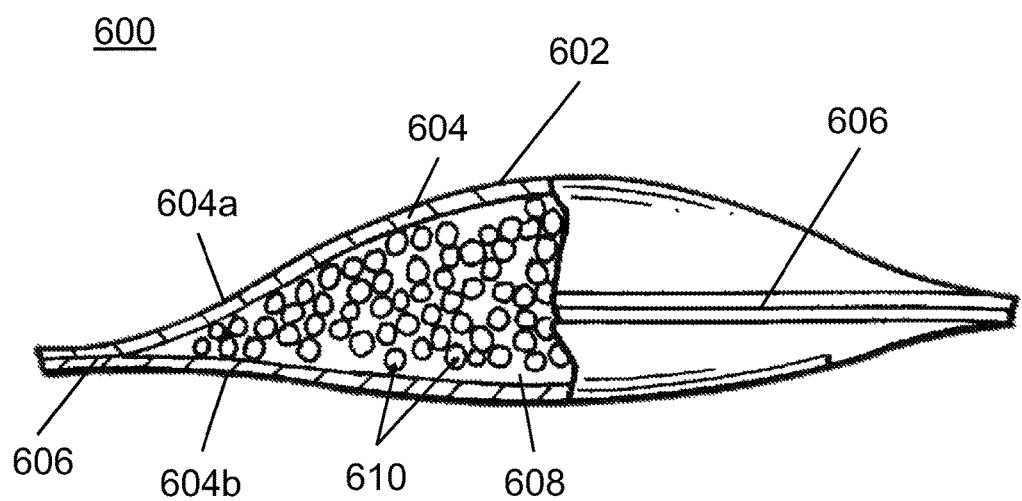
FIG. 6 is a cross-sectional side view of a packet containing the halo active aromatic sulfonamide compounds of the present disclosure in solid form. A flexible housing is made from the porous substrate, which acts as a filter by letting material pass through to contact the sulfonamide compounds contained therein.

The embodiment illustrated in FIG. 6 shows an example where the filter 600 is in the form of a packet. The porous substrate 602 is comprised of one or more layers of a filter medium 604, which may be formed into a flexible housing (in the form of a bag) by any suitable method of manufacture. For example, the filter packet may be formed by sealing the edges 606 of two separate sheets of filter medium material 604a and 604b, completely around aligned perimeters thereof, as depicted in FIG. 6, or alternatively by folding a single rectangular sheet at a midsection thereof and sealing the doubled sheet along the three open edges. Any suitable adhesive may be used to seal the edges 606 of the porous substrate 602 to form the filter packet, or any other means for sealing, including for example stitching, heat sealing, crimping, etc., may alternatively be employed.

The edges 606 of the porous substrate 602 are sealed to form an interior region 608 in which the halo active aromatic sulfonamide organic compound 610 is contained in solid form. In this regard, the halo active aromatic sulfonamide organic compound 610 can be in the form of a solid contiguous, unitary form, as well as granulated or other solid particulate form of halo active aromatic sulfonamide organic compound retained within a confining structure or encapsulated in a water-soluble medium. The halo active aromatic sulfonamide organic compound 610 illustrated in FIG. 6 is shown in granulated form and is confined within sealed edges 606 which define the interior region 608 of the packet 600. It is also contemplated that the halo active aromatic sulfonamide organic compound of the present disclosure can be dispersed on and within the one or more layers of the filter medium 604 for additional odor control, if desired.

The filter packet 600 having the halo active aromatic sulfonamide organic compound in a solid form advantageously eliminates malodors which exist wherever the filter packet is placed and the area surrounding the packet. The filter packet operates to eliminate malodors passively. That is, odorific molecules in an environment move across a concentration gradient by diffusing from an area of higher concentration to an area of lower concentration. As the molecules diffuse, they pass through the one or more layers 604 of the porous substrate 602, where the odorific molecules then contact the solid halo active aromatic sulfonamide organic compound contained within the filter packet. Upon contact, the odorific molecules react with the active compound, thereby reducing and eventually eliminating the odor of the environment where the filter packet is placed.

The packet-type filter 600 shown in FIG. 6 may be placed in any number of environments where it is desirable to eliminate odors, including but not limited to shoes, storage lockers, drawers, cars, boats, etc. The packet-type filter 600 is shown as having a generally pillow-shaped configuration, the specific size of which is dependent upon the nature of the environment in which it is to be used. However, it should be understood that the pillow-shape configuration is only exemplary and the present disclosure should not be limited by particular shapes/sizes identified for the filter packet, and that the packet filter can have any suitable shape/size depending on the application with which it is to be used. For example, the packet may generally be smaller if being used in connection with a shoe, compared to use in an automobile where the packet may be larger.

Figure 7:
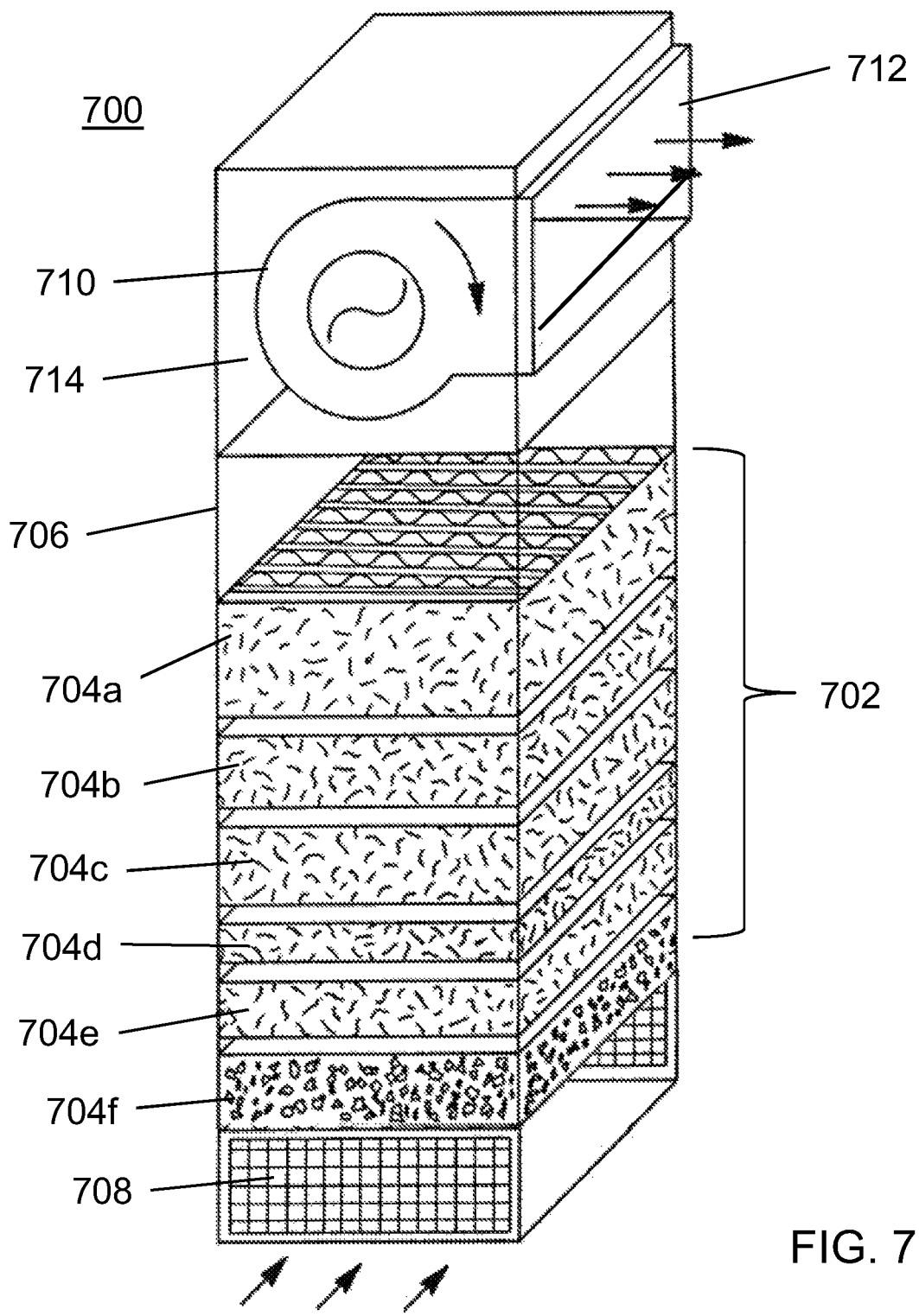
FIG. 7 is a perspective view of a filtration system containing a plurality of filters of the present disclosure.

Any of the aforementioned filters previously described can also be included in a filtration system, such as filtration system 700 illustrated in FIG. 7. The filtration system 700 includes a housing 706 having an inlet 708 and an outlet 712. The housing forms a fluid duct 714 that connects the inlet 708 to the outlet 712, and which is suitable for controlling fluid flow. A blower 710 provides pressure for fluid movement.

The filtration system 700 also includes a filter portion 702 between the inlet 708 and the outlet 712. The filter portion includes one or more slots into which filters can be placed. As illustrated here, there are slots for six filters 704 704a, 704b, 704c, 704d, 704e, 704f. Incoming air enters through the inlet vent 708 and is drawn through the filters disposed within the fluid duct, i.e. in the path of the moving air. The filters can be the same or different, depending on the particular application in which the filtration system 700 is used. For example, the filter 704f can be selected based on an ability to remove larger particles or contaminants from the incoming air, the filter 704a can be chosen based on an ability to remove smaller/fine particles or contaminants, and intermediate filters 704b-704e can be made from a filter medium which removes contaminants/particles larger than those removed by filter 704a but smaller than those removed by filter 704f. Each of the filters 704a, 704b, 704c, 704d, 704e, 704f can be carried in cartridges or other such frames, which slide into receptacles in the apparatus housing, so that they can periodically be removed and replaced.

At least one of the filters 704a, 704b, 704c, 704d, 704e, 704f contains the halo active aromatic sulfonamide organic compound dispersed on a porous substrate. In particular embodiments, the filter closest to the outlet 612 (i.e. filter 704a) is the filter that contains the sulfonamide compound. As a fluid stream (e.g. air, water) passes through the filter portion 702, odorous molecules in the fluid stream react with the active sulfonamide compound, thereby reducing and eventually eliminating the odor of the fluid stream. Furthermore, the odor of the contaminants/particles trapped in the filter portion 702 or other components will be reduced and eventually eliminated.

While the filtration system depicted in FIG. 7 is shown as including six filters in the filter portion, it will be appreciated that any number of filters can be used. Furthermore, the size, shape, spacing, alignment, and positioning of the filters can be selected to accommodate air flow rates and intended use of the filtration system 700. While the filtration depicted in FIG. 7 has a design particularly suited for use with air, it will be appreciated that other fluids (e.g., air, gas, and mixtures of air and liquids) can be used.

The porous substrates described herein can be manufactured from filter media made from raw materials which are natural, inorganic, synthetic (i.e., man-made), or a mixture of natural, inorganic, and synthetic materials. The filter media may also be nonwoven or woven to form the porous substrate. Nonwoven refers to textiles formed by a process where the material fibers are interlocked by mechanical (e.g., friction/entanglement) or chemical (e.g., adhesion) means known in the art. These processes can be used to form composite structures and/or membranes which make up the filter medium of the porous substrate. Common processes to form nonwoven textiles include wet-laid, dry-laid, melt-blown, and spun-laid or spun-bound processes.

Woven refers to textiles formed by a process where material fibers are interlaced by weft (transverse) and warp (longitudinal) fibers or threads. Often the material fibers are first formed into yarn (i.e., long continuous lengths of interlocked fibers) before undergoing the weaving process.

Exemplary natural raw materials for the filter media of the porous substrate include regenerated fibers, such as cellulosic materials made from pulp fiber. Pulp fiber refers generally to a material prepared by chemically or mechanically separating cellulose fibers from wood, fiber crops or waste paper. Common porous substrates made from pulp fiber materials include cellulosic wet-laid products (e.g., paper), acetate, triacetate, rayon, and lyocell. Other natural raw materials include cotton, needle-felt fabric (e.g., wool), and rubber.

Exemplary inorganic raw materials for the filter media of the porous substrate include metallic fibers, metallic substrates, fiberglass, glass, or stainless steel.

Exemplary synthetic raw materials for the filter media of the porous substrate include polymeric materials such as polyvinyl chloride (PVC), polyethylene (PE), polypropylene (PP), fluoropolymer, polytetrafluoroethylene (PTFE), polyethersulfone (PES), nylon, acrylic, polyester, polyolefin, polyvinylidene difluoride (PVDF), polyphenylene sulfide (PPS), polyetherimide (PEI), polyether ether ketone (PEEK), liquid crystal polymer (LCP), aramid fiber, or polyimide fiber.

The filter medium may be formed from fibers that are joined together, or can be solid particles.

The porous substrates described in the present disclosure, and the filter media from which the porous substrates are made, are suitable to filter contaminants/particles from a fluid (e.g., water, air) according to a variety of known filtration classes and corresponding particle size, including coarse screening for removing particles having a size of about 2000 micrometers (μm) or more; coarse filtration of particles about 70 μm to about 2000 μm in size; fine filtration of particles about 0.1 μm to about 70 μm in size; microfiltration of particles having a size of about 0.1 μm to about 1 μm; ultrafiltration of particles with a size of about 0.005 μm to about 0.1 μm; nanofiltration of particles from about 0.001 μm to about 0.005 μm in size; and reverse osmosis filtration of particles having a size of about 0.001 μm or less.

The halo active aromatic sulfonamide compounds used in the filters and with the porous substrate/filter media of the present disclosure have the structure of Formula (I):

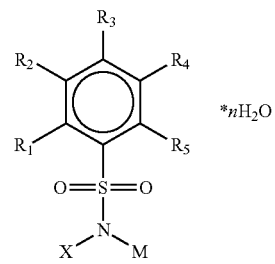

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;

R' is hydrogen, an alkali metal, an alkaline earth metal, substituted $C_1$-$C_{12}$ alkyl, or unsubstituted $C_1$-$C_{12}$ alkyl; and R" is hydrogen or substituted or unsubstituted $C_1$-$C_{12}$ alkyl, where the two R" groups in CON(R")$_2$ may be independently selected;

X is halogen;

M is an alkali or alkaline earth metal; and n is the number of water molecules per molecule of the sulfonamide compound.

It should be noted that the term "aromatic", as used herein, refers to the chemical property of conjugated bonds whose delocalized electrons contribute to the stability of the overall compound, and is not used to refer to a smell detected by the nose.

Generally, M is sodium or potassium. X is generally chlorine, bromine, fluorine, or iodine, and in particular embodiments is chlorine. Compounds of Formula (I) may or may not be hydrated, as indicated by the variable n. In particular embodiments, the compounds of Formula (I) are a trihydrate (i.e., n=3). In other embodiments, the compound is in a solid form, such as a powder.

R' is substituted or unsubstituted $C_1$-$C_{12}$ alkyl. R" is hydrogen or substituted or unsubstituted $C_1$-$C_{12}$ alkyl, and the two R" groups in the CON(R")$_2$ may be independently selected.

When the phenyl and/or alkyl group is substituted, one or more hydrogen atoms may be independently replaced with hydroxyl or halogen.

In some embodiments of Formula (I), at least two of $R_1$, $R_2$, $R_3$, $R_4$, and $R_5$ are not hydrogen.

In particular embodiments of Formula (I), $R_3$ is COOH, or COOM$_1$; $R_1$, $R_2$, $R_4$, and $R_5$ are independently selected from hydrogen, COOH, COOM$_1$, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl; X is halogen; K is an alkali or alkaline earth metal; and n is the number of water molecules per molecule of the sulfonamide compound.

In further embodiments, $R_3$ is COOH, or COOM$_1$; $R_1$, $R_2$, $R_4$, and $R_5$ are independently selected from hydrogen, COOH, COOM$_1$, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl; X is halogen; M is an alkali or alkaline earth metal; n is the number of water molecules per molecule of the sulfonamide compound; and at least one of $R_1$, $R_2$, $R_4$, and $R_5$ is not hydrogen.

In other embodiments of Formula (I), the halo active aromatic sulfonamide compound has the structure of Formula (II):

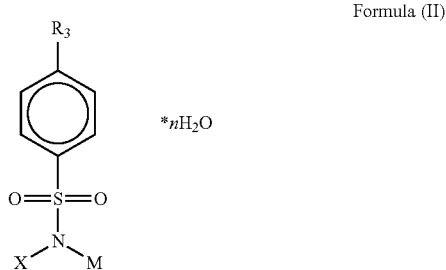

Formula (II)

wherein $R_3$ is COOR'; R' is hydrogen, an alkali metal, an alkaline earth metal, substituted $C_1$-$C_{12}$ alkyl, or unsubstituted $C_1$-$C_{12}$ alkyl; X is halogen; M is an alkali or alkaline earth metal; and n is the number of water molecules per molecule of the sulfonamide compound. The N-chloro-4-carboxybenzenesulfonamide compound of Formula (II) is also referred to herein as BENZ. BENZ exhibits a lower chlorine smell than chloramine-T or chloramine-B. When BENZ is combined with at least one fragrance, there is no detectable chlorine smell for most humans. BENZ has other favorable properties such as higher solubility in water, greater product stability, ease of formulation, wider pH range, etc.

In yet other embodiments of Formula (I), $R_3$ is selected from COOH, COOM$_1$, COOR', CON(R")$_2$, CN, NO$_2$, and halogen; $R_1$, $R_2$, $R_4$, and $R_5$ are independently selected from hydrogen, COOH, COOM$_1$, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl; X is halogen; M is an alkali or alkaline earth metal; and n is the number of water molecules per molecule of the sulfonamide compound.

In still other embodiments of Formula (I), $R_1$, $R_2$, $R_3$, $R_4$, and $R_5$ are independently selected from hydrogen, COOH, COOM$_1$, NO$_2$, or halogen; $R_1$, $R_2$, $R_4$, and $R_5$ can additionally be independently selected from substituted or unsubstituted $C_1$-$C_{12}$ alkyl; X is halogen; M is an alkali or alkaline earth metal; and n is the number of water molecules per molecule of the sulfonamide compound.

In yet other embodiments of Formula (I), $R_2$ and $R_4$ are identical to each other; and $R_1$, $R_3$, and $R_5$ are hydrogen.

In yet other embodiments of Formula (I), $R_2$ and $R_4$ are hydrogen; and $R_1$, $R_3$, and $R_5$ are identical to each other.

In more specific embodiments of Formula (I), $R_3$ is selected from COOH, COOM$_1$, COOR', and CON(R")$_2$. Most desirably, $R_3$ is COOH or COOM$_1$, while $R_1$, $R_2$, $R_4$, and $R_5$ are hydrogen.

In still other embodiments of Formula (I), $R_3$ is COOH or COOM$_1$; $R_1$, $R_2$, $R_4$, and $R_5$ are independently selected from hydrogen, NO$_2$, halogen, and substituted or unsubstituted $C_1$-$C_{12}$ alkyl; X is halogen; M is an alkali or alkaline earth metal; and n is the number of water molecules per molecule of the sulfonamide compound. In further specific embodiments, at least one of $R_1$, $R_2$, $R_4$, and $R_5$ is not hydrogen.

The halo active aromatic sulfonamide compounds of Formula (I) are stable and do not decompose in aqueous solution, allowing the porous substrate to have a long shelf life. The compounds of Formula (I) are also very soluble in water, low in toxicity, and have minimal bleach odor.

There may be a total of about 0.0001 grams (i.e. 1 milligram) to about 10.0 grams (i.e. 1000 milligrams) of the halo active aromatic sulfonamide compound per gram of the porous substrate. In further embodiments, the amount of the sulfonamide compound may be about 1 mg to about 100 mg, or from about 20 mg to about 10000 mg, or from about 40 mg to about 6000 mg, or from about 100 mg to about 5000, or from about 300 mg to about 4000 mg, all measured per gram of the porous substrate. Put another way, the amount of the halo active aromatic sulfonamide compound can be from about 0.00001 to about 0.99 wt % of the porous substrate, or from about 0.09 wt % to about 9.5 wt %, or from about 1.5 wt % to about 95 wt %, or from about 3 wt % to about 90 wt %, or from about 9 wt % to about 85 wt %, or from about 20 wt % to about 80 wt %. Again, it is particularly contemplated that the active sulfonamide compound is in the form of a dry solid powder.

For stability and for optimum performance, the pH of the odor-controlling composition should be between 6 and 14, though generally the pH should be kept between 7 and 9.

In order to maintain the solution within these pH ranges, a buffering agent may be present. The buffering agent can compensate for any change in pH that may result from the acidity of the contaminants, the conditions of application, the type of porous substrate or filter medium, and/or the nature of the odor causing molecule. Exemplary buffering agents include sodium bicarbonate, potassium bicarbonate, sodium carbonate, potassium carbonate, acetate buffers (such as sodium acetate), phosphate buffers (such as tri and di sodium phosphate and mixtures thereof, pH blended phosphates, sulfate buffers (such as di and tri sodium sulfate), and mixtures thereof. The buffering agent can be added up to the limit of solubility of the odor-controlling composition that is used to apply the halo active aromatic sulfonamide compound. In particular embodiments, the preferred weight ratio of the sulfonamide compound to the buffering agent is from about 50:1 to about 1:1, or from about 50:1 to about 2:1, or from about 20:1 to about 2:1. The preferred buffering agent is sodium bicarbonate.

The use of the bicarbonates in the disclosed compositions also appears to decrease color which may be due to pH effects. In particular, bicarbonates reduce the yellow/green color of BENZ solutions drastically. This effect may be highly desirable in some applications where a yellow color is disfavored.

Upon removal of the filter from the filtration system, the filter now contains much higher levels of contaminants due to use. The active sulfonamide compound will continue to react with and reduce the level of malodorous molecules, reducing unwanted odor even further. The active sulfonamide compound continues to actively react with odor-causing molecules over extended periods of time. Even after active use is finished, the odor of treated filters continues to decrease. Treated filters show improved effect over time. Filters used for extended time have built-in protection even after extended periods. This is extremely useful for the consumer, as frequent filter changes are not necessary until the filters reach the end of their life span. In this regard, the active sulfonamide compound can continue to reduce odors in an environment over a period of time which corresponds to the life span of the filters. Further, as the treated filters continue to reduce odors after removal, disposal of the product is neither evident nor obvious, as the formulation continues to work.

In other embodiments, the sulfonamide compound is encapsulated. More specifically, the sulfonamide compound may be encapsulated (i.e. form a core) in a water-soluble medium (i.e. a shell around the core), resulting in a particle with a core-shell structure. The buffering agent can be part of the core as well, or can remain outside the water-soluble medium. Upon contact with gas or liquid, the medium encapsulating the sulfonamide compound will slowly dissolve to release the sulfonamide compound, which can then react with malodorous molecules. It is contemplated that the water-soluble medium could be a shell, or a gel, or a liquid, as appropriate for the application.

Generally, an odor-controlling composition containing the sulfonamide compound is applied to the filter, porous substrate, or filter medium by dipping, spraying, or washing. For example, the sulfonamide compound may be mixed with water or another solvent to form an aqueous or other solution, along with the buffering agent. The sulfonamide compound may range from about 0.01% to 30% (w/v) of the aqueous solution, i.e. about 0.01 to about 30 grams of the sulfonamide compound per milliliter (g/mL) of the aqueous solution. The solution is applied to the filter, filter medium, or porous substrate. The solvent is then allowed to evaporate, leaving behind the active sulfonamide compound. Multiple sprays can be used to increase the amount of active sulfonamide compound.

It has been found that due to the stable and hydrated nature of the structure, the sulfonamide compound will activate only when a malodorous molecule is encountered. Minor amounts of water, either through the hydrated active sulfonamide compound and/or the ambient humidity, are sufficient for the sulfonamide to bond with the odor-causing molecules even at ppm and ppb levels.

It has been found that the raw materials that go into making a filter, such as the non-wovens, polymeric fibers, gaskets, seals, in addition to other components with which the filter cooperates in a filtration system, such as transport structures (e.g., ducts), etc., can themselves have a distasteful odor. It is contemplated that these raw materials, parts, and additional components can also be treated with the odor-controlling composition, so that they do not emit malodorous molecules. Once incorporated additional components, the sulfonamide compound begins to eliminate the odor-causing molecules. Because of the hydrated nature of the sulfonamide compound and the ambient air conditions, there is enough interaction at the ppm and ppb level to effectively control the odors emanating from the otherwise solid materials. Such odors can be removed, eliminated, and/or reduced prior to the filter parts being combined or manufactured into a finished filter or filtration system.

When being used, the active sulfonamide compound present in the filter or filtration system is activated by coming into contact with fluids (e.g., gas or liquids such as air and water) which may include odorific molecules. The sulfonamide compound can be chemically activated and then released over time to reduce the odor-causing molecules.

Upon removal of the filter from the filtration system, the filter now contains much higher levels of contaminants due to use. The active sulfonamide compound will continue to react with and reduce the level of malodorous molecules, reducing unwanted odor even further. The active sulfonamide compound continues to actively react with odor-causing molecules over extended periods of time. Even after active use is finished, the odor of treated filters continues to decrease. Treated filters show improved effect over time. Filters used for extended time have built-in protection even after extended periods. This is extremely useful for the consumer, as frequent filter changes are not necessary until the filters reach the end of their life span. In this regard, the active sulfonamide compound can continue to reduce odors in an environment over a period of time which corresponds to the life span of the filters. Further, as the treated filters continue to reduce odors after removal, disposal of the product is neither evident nor obvious, as the formulation continues to work.

The odor controlling composition containing the active sulfonamide compound may be applied to materials of construction prior to filter/filtration system construction or during the construction of the filter/filtration system. Prior to using the odor controlling composition in the materials for construction, the composition may be used to either remove raw material malodors or pre-treat raw materials so that the odor controlling composition is on "stand by" when odor molecules are encountered.

Raw materials may not be pre-treated only prior to filter/filtration system construction, but they may also be strategically treated during construction of the product. Varying components may be treated such that there is strategically placed odor control, or multiple components may be treated thereby creating a synergistic effect of all-encompassing odor control.

The odor controlling compositions used to make the odor-controlling filters described herein can be formulated to deliver varying levels of odor control depending on the type of raw material, the location of the filter in a filtration system, and the type of desired odor control, for example, residential (e.g., home HVAC systems, etc.), commercial (e.g., hotels, gyms, restaurants, businesses, etc.), industrial (e.g., factories, emissions, pollution, water purification, etc.), transportation modes (e.g., personal automobiles, airplanes, buses, boats/ships, trains, etc.), and consumer goods (e.g., appliances such as vacuum cleaners, refrigerators/freezers, electronics, etc.). The odor controlling composition may further be in the form of a liquid or a solid or any form in between such as a gel or semi-solid, and may be added alone or in conjunction with a solvent. The solvent may be water, alcohol, or another solvent.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A filter, comprising:
a porous substrate made from one or more layers of a filter medium that contain a halo active aromatic sulfonamide compound of Formula (I):

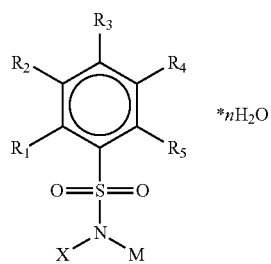

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;
R' is hydrogen, an alkali metal, an alkaline earth metal, substituted $C_1$-$C_{12}$ alkyl, or unsubstituted $C_1$-$C_{12}$ alkyl; and
R" is hydrogen or substituted or unsubstituted $C_1$-$C_{12}$ alkyl, where the two R" groups in CON(R")$_2$ may be independently selected;
X is halogen;
M is an alkali or alkaline earth metal; and
n is the number of water molecules per molecule of the sulfonamide compound; and
a first support structure on one side of the porous substrate and a second support structure on an opposite side of the porous substrate, wherein the halo active aromatic sulfonamide compound of Formula (I) is also dispersed on the first support structure and the second support structure.

2. The filter of claim 1, wherein the halo active aromatic sulfonamide compound is present in the amount of about 0.0001 to about 10.0 grams per gram of the substrate.

3. The filter of claim 1, wherein the filter medium is made from a natural material, an inorganic material, a synthetic material, or a mixture thereof.

4. The filter of claim 3, wherein the filter medium is woven or nonwoven.

5. The filter of claim 1, wherein the filter medium is formed from regenerated fibers of a cellulosic material comprising wet-laid media, acetate, triacetate, rayon, or lyocell.

6. The filter of claim 1, wherein the filter medium fiber is a polymeric material comprising polyvinyl chloride (PVC), polyethylene (PE), polypropylene (PP), fluoropolymer, polytetrafluoroethylene (PTFE), polyethersulfone (PES), nylon, acrylic, polyester, polyolefin, polyvinylidene difluoride (PVDF), polyphenylene sulfide (PPS), polyetherimide (PEI), polyether ether ketone (PEEK), liquid crystal polymer (LCP), aramid fiber, or polyimide fiber.

7. The filter of claim 1, wherein the filter medium is made from metal, fiberglass, glass, or stainless steel.

8. The filter of claim 1, wherein the filter medium is made from cotton, needle-felt fabric, or rubber.

9. The filter of claim 1, wherein the halo active aromatic sulfonamide compound is a solid or is encapsulated in a water-soluble medium.

10. The filter of claim 9, wherein the halo active aromatic sulfonamide compound is contained within a packet formed by the one or more layers of filter medium that make up the porous substrate.

11. The filter of claim 1, wherein the porous substrate is pleated or is flat.

12. The filter of claim 1, further comprising a frame surrounding the porous substrate.

13. The filter of claim 1, wherein the halo active aromatic sulfonamide compound is applied to the filter medium in the form of a solution and is present in the solution in an amount of from about 0.01% to 30% (w/v).

14. A method of reducing odor from a fluid stream, comprising:
passing a fluid stream containing odorific molecules through a filter;
wherein the filter comprises (A) a porous substrate made from one or more layers of a filter medium that contain a halo active aromatic sulfonamide compound of Formula (I):

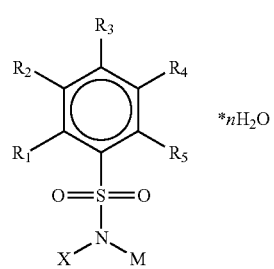

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;
R' is hydrogen, an alkali metal, an alkaline earth metal, substituted $C_1$-$C_{12}$ alkyl, or unsubstituted $C_1$-$C_{12}$ alkyl; and
R" is hydrogen or substituted or unsubstituted $C_1$-$C_{12}$ alkyl, where the two R" groups in CON(R")$_2$ may be independently selected;
X is halogen;
M is an alkali or alkaline earth metal; and
n is the number of water molecules per molecule of the sulfonamide compound; and (B) a first support structure on one side of the porous substrate and a second support structure on an opposite side of the porous substrate, wherein the halo active aromatic sulfonamide compound of Formula (I) is also dispersed on the first support structure and the second support structure.

15. The method of claim 14, wherein the fluid stream is a liquid fluid stream or a gas fluid stream.

16. The method of claim 14, wherein the odor is reduced during a life span of the filter.

17. The method of claim 14, wherein the odorific molecules are sulfur-containing odorific molecules or nitrogen-containing odorific molecules.

18. The method of claim 14, wherein the porous substrate captures particles having a size of about 2000 μm, or from about 70 μm to about 2000 μm, or from about 0.1 μm to about 70 μm, or from about 0.1 μm to about 1 μm, or from about 0.005 μm to about 0.1 μm, or from about 0.001 μm to about 0.005 μm, or about 0.001 μm.

19. The method of claim 14, wherein $R_1$, $R_2$, $R_4$, and $R_5$ are hydrogen, and $R_3$ is COOM, wherein M is an alkali or alkaline earth metal.

20. A filtration system, comprising:
a fluid duct for transporting a fluid stream containing odorous molecules; and
a filter disposed within the fluid duct that comprises a porous substrate made from one or more layers of a filter medium, a first support structure on one side of the porous substrate, and a second support structure on an opposite side of the porous substrate;
wherein a halo active aromatic sulfonamide compound is contained on the filter medium, the first support structure, and the second support structure, the halo active aromatic sulfonamide compound having the structure of Formula (I):

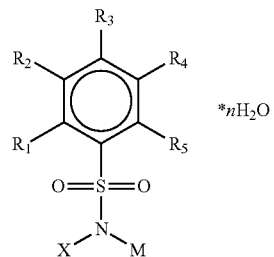

Formula (I)

wherein $R_1$, $R_2$, $R_3$, $R_4$, and $R_5$ are independently selected from hydrogen, COOR', CON(R")$_2$, alkoxy, CN, NO$_2$, SO$_3$R", halogen, substituted or unsubstituted phenyl, sulfonamide, halosulfonamide, and substituted or unsubstituted $C_1$-$C_{12}$ alkyl;

R' is hydrogen, an alkali metal, an alkaline earth metal, substituted $C_1$-$C_{12}$ alkyl, or unsubstituted $C_1$-$C_{12}$ alkyl; and R" is hydrogen or substituted or unsubstituted $C_1$-$C_{12}$ alkyl, where the two R" groups in CON(R")$_2$ may be independently selected;

X is halogen;

M is an alkali or alkaline earth metal; and n is the number of water molecules per molecule of the sulfonamide compound.

21. The filtration system of claim 20, wherein the fluid duct and the filter are located in an HVAC system, an automobile, a water filtration unit, an industrial or commercial filtration unit, a vacuum cleaner or other household cleaning device.

* * * * *